US012782301B2

(12) United States Patent
Zeng et al.

(10) Patent No.: US 12,782,301 B2
(45) Date of Patent: Nov. 3, 2026

(54) METHODS AND COMPOSITIONS FOR IDENTIFYING CATECHOLAMINE-TYPE STRUCTURES TO ASSESS RESPONSE TO LOW SALINITY ENHANCED OIL RECOVERY

(71) Applicant: BP CORPORATION NORTH AMERICA INC., Houston, TX (US)

(72) Inventors: Huang Zeng, Houston, TX (US); Christianne Clare Wicking, Reading (GB); Nathalia Tessarolo, Middlesex (GB); John William Couves, Bourne End (GB); Ian Ralph Collins, Middlesex (GB)

(73) Assignee: BP CORPORATION NORTH AMERICA INC., Houston, TX (US)

( * ) Notice: Subject to any disclaimer, the term of this patent is extended or adjusted under 35 U.S.C. 154(b) by 735 days.

(21) Appl. No.: 18/039,012

(22) PCT Filed: Dec. 1, 2021

(86) PCT No.: PCT/US2021/061405
§ 371 (c)(1),
(2) Date: May 26, 2023

(87) PCT Pub. No.: WO2022/119920
PCT Pub. Date: Jun. 9, 2022

(65) Prior Publication Data

US 2023/0358694 A1 Nov. 9, 2023

Related U.S. Application Data

(60) Provisional application No. 63/120,187, filed on Dec. 1, 2020.

(51) Int. Cl.

| | |
|---|---|
| ***G01N 33/24*** | (2006.01) |
| ***E21B 25/00*** | (2006.01) |

(Continued)

(52) U.S. Cl.
CPC ....... *G01N 23/2055* (2013.01); *E21B 25/005* (2013.01); *G01N 33/24* (2013.01);
(Continued)

(58) Field of Classification Search
CPC .. G01N 33/24; G01N 33/241; G01N 23/2055; G01N 2223/616; E21B 25/005;
(Continued)

(56) References Cited

U.S. PATENT DOCUMENTS

| | | | |
|---|---|---|---|
| 3,208,528 | A | 9/1965 | Elliott et al. |
| 5,741,707 | A | 4/1998 | Herron et al. |

FOREIGN PATENT DOCUMENTS

| | | | |
|---|---|---|---|
| WO | 2017/162489 | A1 | 9/2017 |
| WO | 2019/034756 | A1 | 2/2019 |

OTHER PUBLICATIONS

Field, E. et al, Industrial and Engineering Chemistry 1940, 32, 489-496. (Year: 1940).*

(Continued)

*Primary Examiner* — Arlen Soderquist
(74) *Attorney, Agent, or Firm* — CONLEY ROSE, P.C.

(57) ABSTRACT

A method of assessing the response of a reservoir rock to low salinity water includes obtaining a formation core sample of a reservoir rock from a reservoir. In addition, the method includes sequentially washing the formation core sample with a first series of solvents to form a first series of solvent extracts and an extracted formation core sample. Further, the method includes sequentially washing the extracted formation core sample with a second series of solvents to form a second series of solvent extracts and a cleaned formation core sample. The method also includes generating a series of mass spectra of the second series of solvent extracts. The relative abundance of the catecholamine-type structures (CTS) is determined using the (Continued)

series of mass spectra. Still further, the method includes subjecting the formation core sample to analysis by X-ray diffraction to generate a diffraction pattern. The relative abundance of kalonite is determined using the diffraction pattern. Moreover, the method includes assessing a response of the reservoir rock to low salinity water based on the percentage of kalonite and the relative abundance of CTS.

19 Claims, 7 Drawing Sheets

(51) Int. Cl.
*G01N 23/2055* (2018.01)
*H01J 49/16* (2006.01)
*E21B 43/20* (2006.01)

(52) U.S. Cl.
CPC ............ *H01J 49/161* (2013.01); *E21B 43/20* (2013.01); *G01N 2223/616* (2013.01)

(58) Field of Classification Search
CPC ......... E21B 43/20; H01J 49/161; H01J 49/26; Y10T 436/24
USPC ............................................ 436/29, 31, 180
See application file for complete search history.

(56) References Cited

OTHER PUBLICATIONS

Snyder L. R., Analytical Chemistry 1969, 41, 314-323. (Year: 1969).*
Grist, D. M. et al, Journal of Canadian Petroleum Technology 1975, 48-52. (Year: 1975).*
Oka, Y. et al, Chemical and Pharmaceutical Bulletin 1977, 25, 632-639. (Year: 1977).*
Baldwin, B. A., SPE Formation Foundation 1988, 125-130. (Year: 1988).*
Hirasaki, G. J. et al, SPE 20506, 1990, 361-375. (Year: 1990).*
Kerwin, J. L., Journal of Mass Spectrometry 1996, 31, 1429-1439. (Year: 1996).*
Schwark, L. et al, Organic Geochemistry 1997, 26, 19-31. (Year: 1997).*
Mueller E. et al, Organic Geochemistry 1998, 28, 625-631. (Year: 1998).*
Rudzinski, W. et al, Energy & Fuels 2000, 14, 464-475. (Year: 2000).*
Tomczyk, N. A. et al, Energy & Fuels 2001, 15, 1498-1504. (Year: 2001).*
Vuorensola, K. et al, Journal of Chromatography A 2002, 979, 179-189. (Year: 2002).*
Zhang, Y, et al, Energy & Fuels 2011, 25, 5083-5089. (Year: 2011).*
Matthiesen, J. et al, Energy & Fuels 2014, 28, 4849-4858. (Year: 2014).*
Abia, R. O., Masters Thesis 2017, 118 pages. (Year: 2017).*
Sanyal, S. et al, Energy & Fuels 2017, 31, 11627-11639. (Year: 2017).*
Zhang, Q. et al, Royal Society Open Science 2018, 5 Article 171492, 12 pages. (Year: 2018).*
Wicking, C. et al, Fuel 2020, 276, Article 118062, 14 pages. (Year: 2020).*
Collins, I.R et al., "Effect of Low Salinity Waterflooding on the Chemistry of the Produced Crude Oil," SPE Improved Oil Recovery Conference, Tulsa, Oklahoma, USA, Apr. 14, 2018, SPE-190191-MS (17 p.).
PCT/US2021/061405 International Search Report and Written Opinion dated Mar. 7, 2022 (17 p.).
Aksulu, Hakan et al., "Evaluation of Low-Salinity Enhanced Oil Recovery Effects in Sandstone: Effects of the Temperature and pH Gradient," Energy & Fuels, vol. 26, No. 6, Jun. 21, 2012, pp. 3497-3503 (7 p.).
Chavan, Mukul et al., "Low-Salinity-Based Enhanced Oil Recovery Literature Review and Associated Screening Criteria," Petroleum Science, vol. 16, No. 6, May 28, 2019, pp. 1344-1360 (17 p.).
Guo, Junhua et al, "Data Report: Refined Method for Calculating Percentages of Kaolinite and Chlorite from X-Ray Diffraction Data, with Application to the Nankai Margin of Southwest Japan," Proceedings of the Integrated Ocean Drilling Program, vol. 314/315/316, Nov. 4, 2011 (14 p.).
PCT/US2021/061405 Response to Written Opinion dated Mar. 7, 2022 and Article 19 Amendments; Response filed Apr. 26, 2022 (16 p.).
Zeng, Huang et al., ""Sticky Molecules" on Rock Surface Might Play an Important Role in Formation Damage due to Asphaltene Deposition," Fuel, vol. 277, No. 117983, 2020 (9 p.).

* cited by examiner

METHODS AND COMPOSITIONS FOR IDENTIFYING CATECHOLAMINE-TYPE STRUCTURES TO ASSESS RESPONSE TO LOW SALINITY ENHANCED OIL RECOVERY

CROSS-REFERENCE TO RELATED APPLICATIONS

This application is a 35 U.S.C. § 371 national stage application of PCT/US2021/061405 filed Dec. 1, 2021 and entitled "Methods and Compositions for Low Salinity Enhanced Oil Recovery," which claims priority under 35 U.S.C. § 119(e) to U.S. Provisional Patent Application No. 63/120,187 filed on Dec. 1, 2020 and entitled "Methods and Compositions for Low Salinity Enhanced Oil Recovery," each of which is hereby incorporated herein by reference in its entirety for all purposes.

STATEMENT REGARDING FEDERALLY SPONSORED RESEARCH OR DEVELOPMENT

Not applicable.

TECHNICAL FIELD

The present disclosure relates generally to systems and methods for enhanced oil recovery (EOR). More particularly, the present disclosure relates to compositions and methods for assessing a reservoir rock response to low salinity water.

BACKGROUND

Waterflooding is one of the most common and widely used oil recovery methods practiced in the oil industry since the 1930s. Conventionally, waterflooding has been considered as a physical oil recovery process that serves two primary functions: (1) to maintain reservoir pressure, and (2) to displace oil from the reservoir pore space toward the producing well by viscous forces.

Low salinity waterflooding is an FOR method in which the salinity of the injected brine during a waterflood is reduced to below about 10,000 ppm total dissolved solids (TDS). The salinity reduction causes production of additional oil. It is thought that the FOR from low salinity waterflooding is dependent on a complex relationship between the salinity, composition of the crude oil in place, and the minerals present in the reservoir. However, the mechanism is widely debated in the open literature and not fully agreed upon. It is generally accepted that low salinity waterflooding leads to a wettability alteration of the rock surface, but the underlying microscopic mechanism is still not entirely understood. An ongoing need exists for novel methods and compositions for assessing the effectiveness of an enhanced oil recovery operation.

SUMMARY

Disclosed herein is a method of assessing the response of a reservoir rock to low salinity water comprising obtaining a formation core sample of a reservoir rock from a reservoir; sequentially washing the formation core sample with a first series of solvents to form a first series of solvent extracts and an extracted formation core sample; sequentially washing the extracted formation core sample with a second series of solvents to form a second series of solvent extracts and a cleaned formation core sample; generating a series of mass spectra of the second series of solvent extracts, wherein the relative abundance of the catecholamine-type structures (CTS) is determined using the series of mass spectra; subjecting the formation core sample to analysis by X-ray diffraction to generate a diffraction pattern, wherein the relative abundance of kalonite is determined using the diffraction pattern; and assessing a response of the reservoir rock to low salinity water based on the percentage of kalonite and the relative abundance of CTS.

Also disclosed herein is a method of enhanced oil recovery from a resource-containing reservoir zone comprising obtaining a rock sample from the resource-containing reservoir zone; contacting the rock sample with solvents sequentially to form solvent extracts and a cleaned rock sample; subjecting the cleaned rock sample to X-ray diffraction wherein X-ray diffraction identifies a percentage kaolinite of the cleaned rock sample; subjecting the solvent extracts to mass spectrometry wherein the mass spectrometry identifies a percentage catecholamine-type structures (CTS) in at least one of the solvent extracts; and determining the reservoir rocks with high possibility of carrying positive response to low salinity water enhanced oil recovery method based on the percentage of kaolinite and the percentage of CTS.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of various exemplary embodiments, reference will now be made to the accompanying drawings, wherein like reference numerals represent like parts.

DETAILED DESCRIPTION

Figure 1:
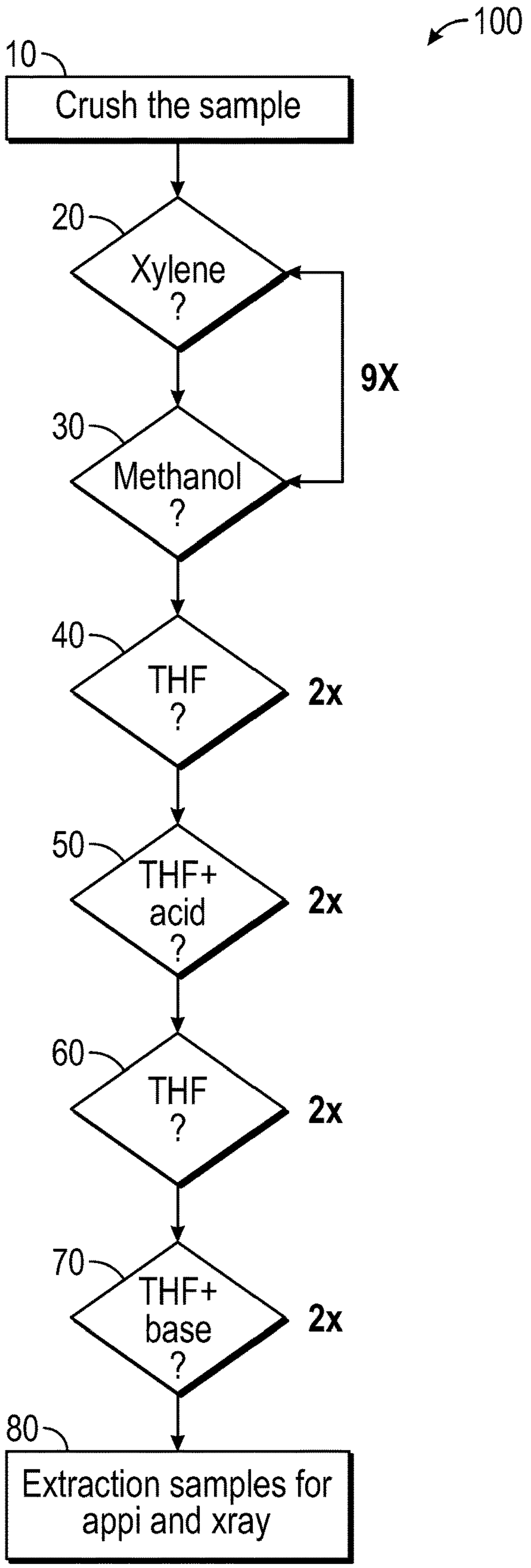
FIG. 1 is a process flow diagram illustrating an embodiment of a method for obtaining samples for testing.
Figure 2A:
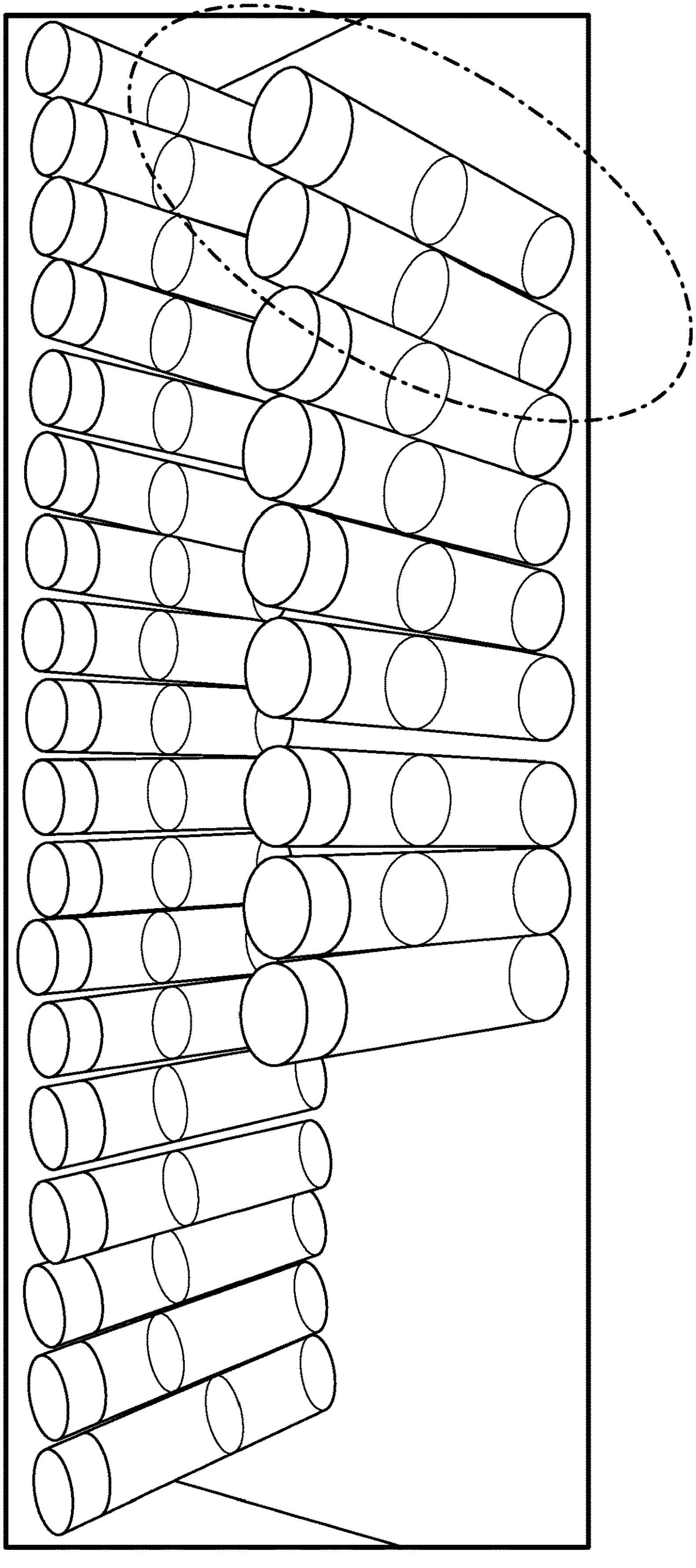
FIG. 2A is a schematic depiction of a sample test for a low salinity response.
Figure 2B:
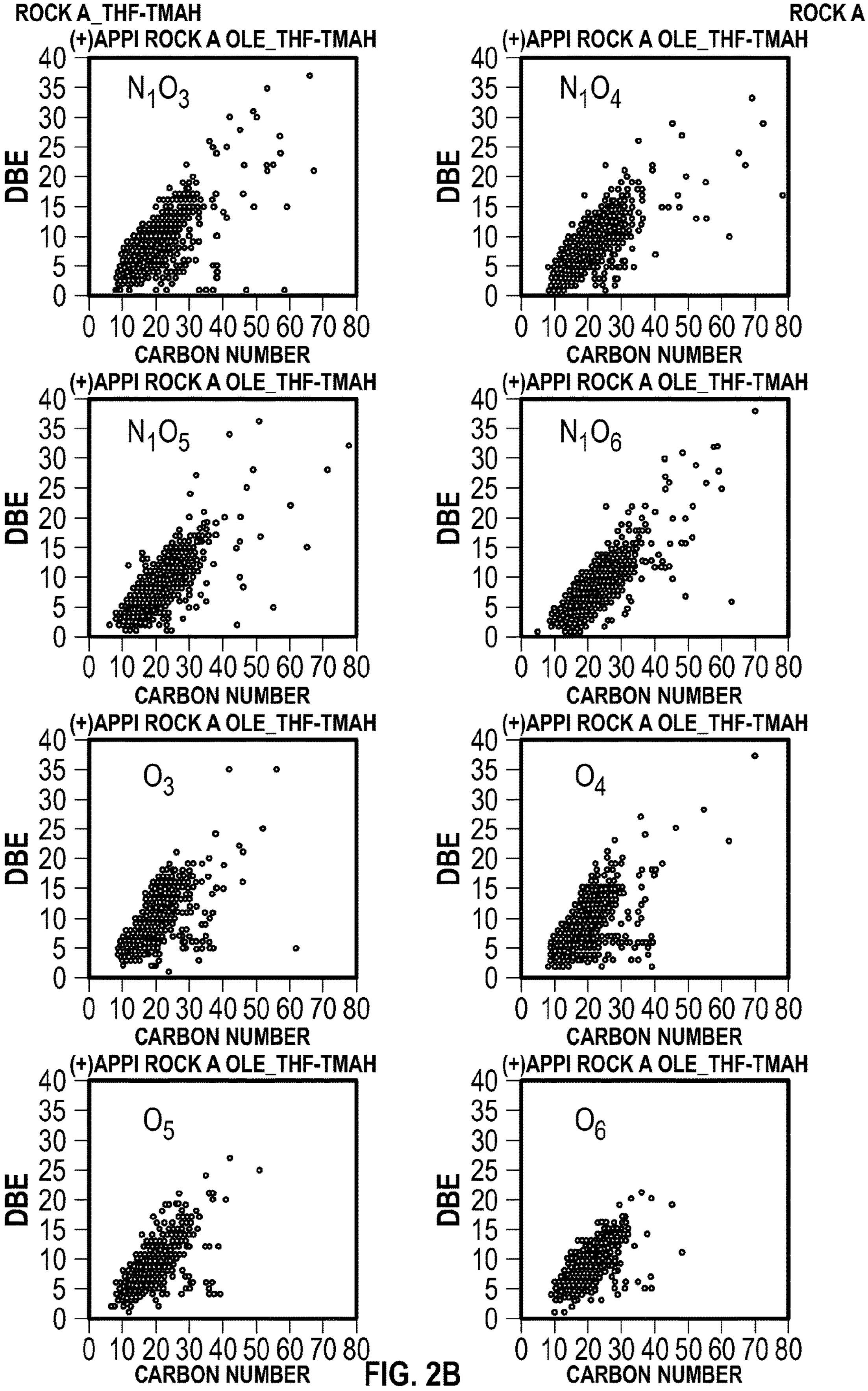
FIGS. 2B-2E are compilations of mass spectra for various rock samples treated as disclosed herein.
Figure 2C:
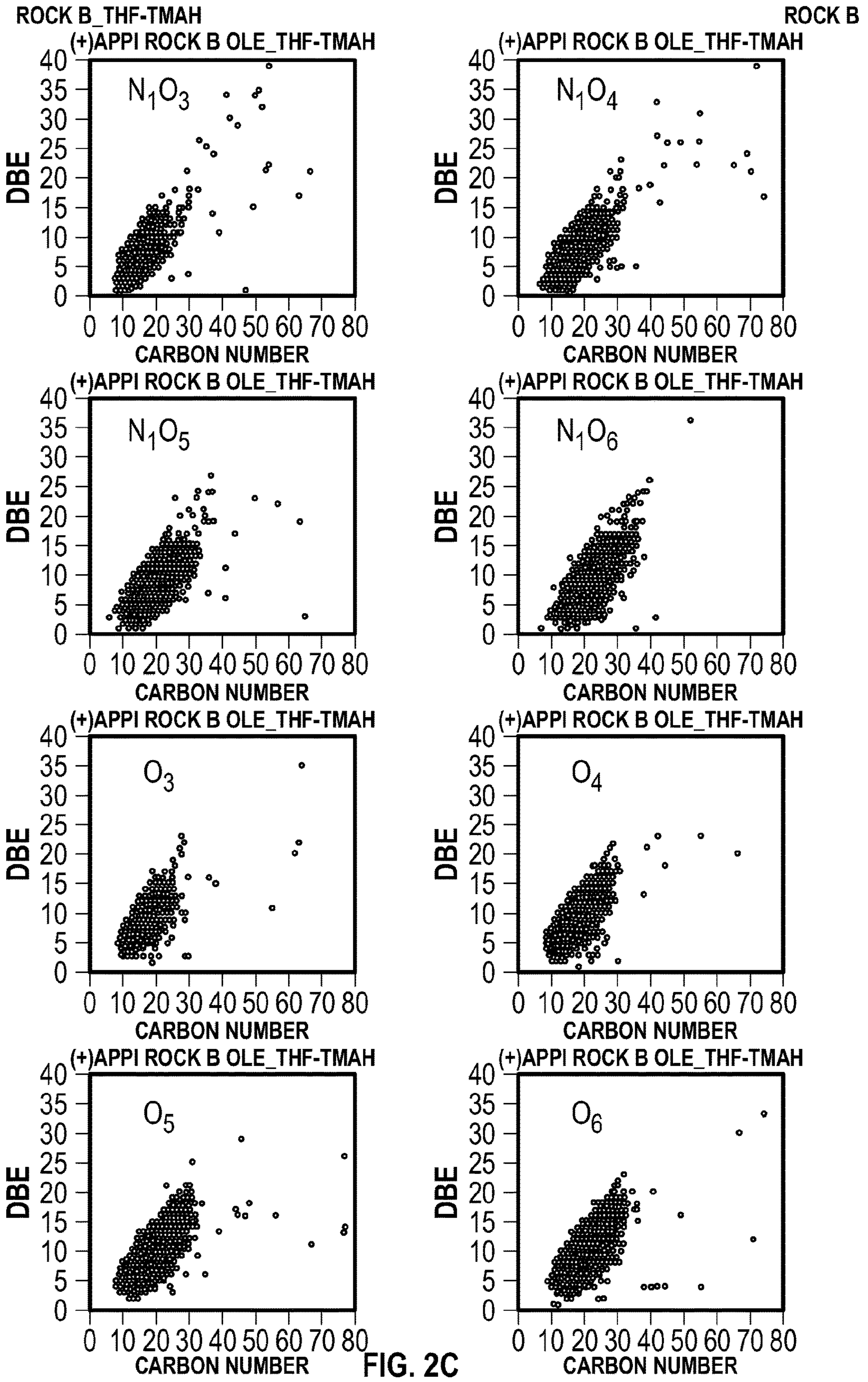
Figure 2D:
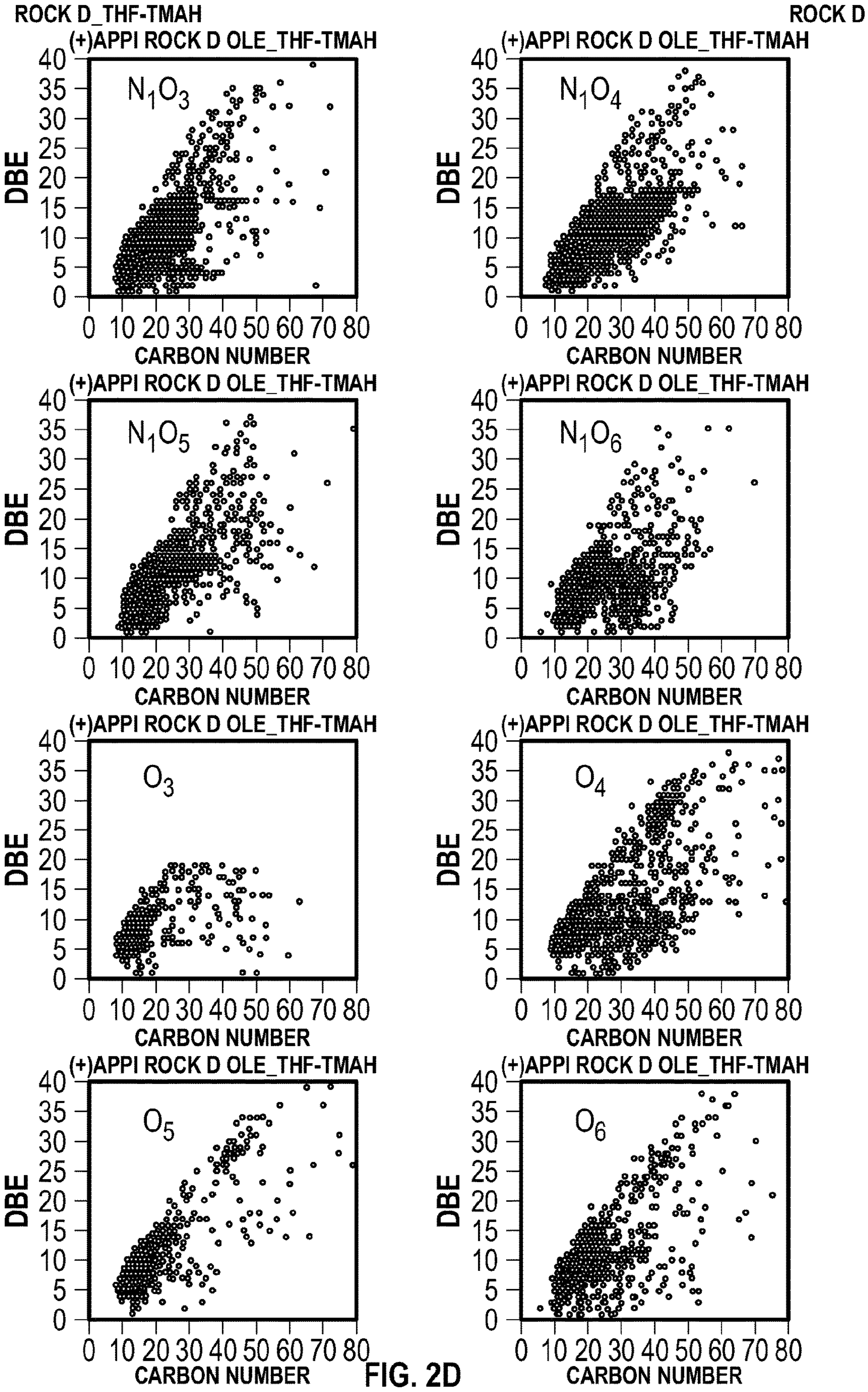
Figure 2E:
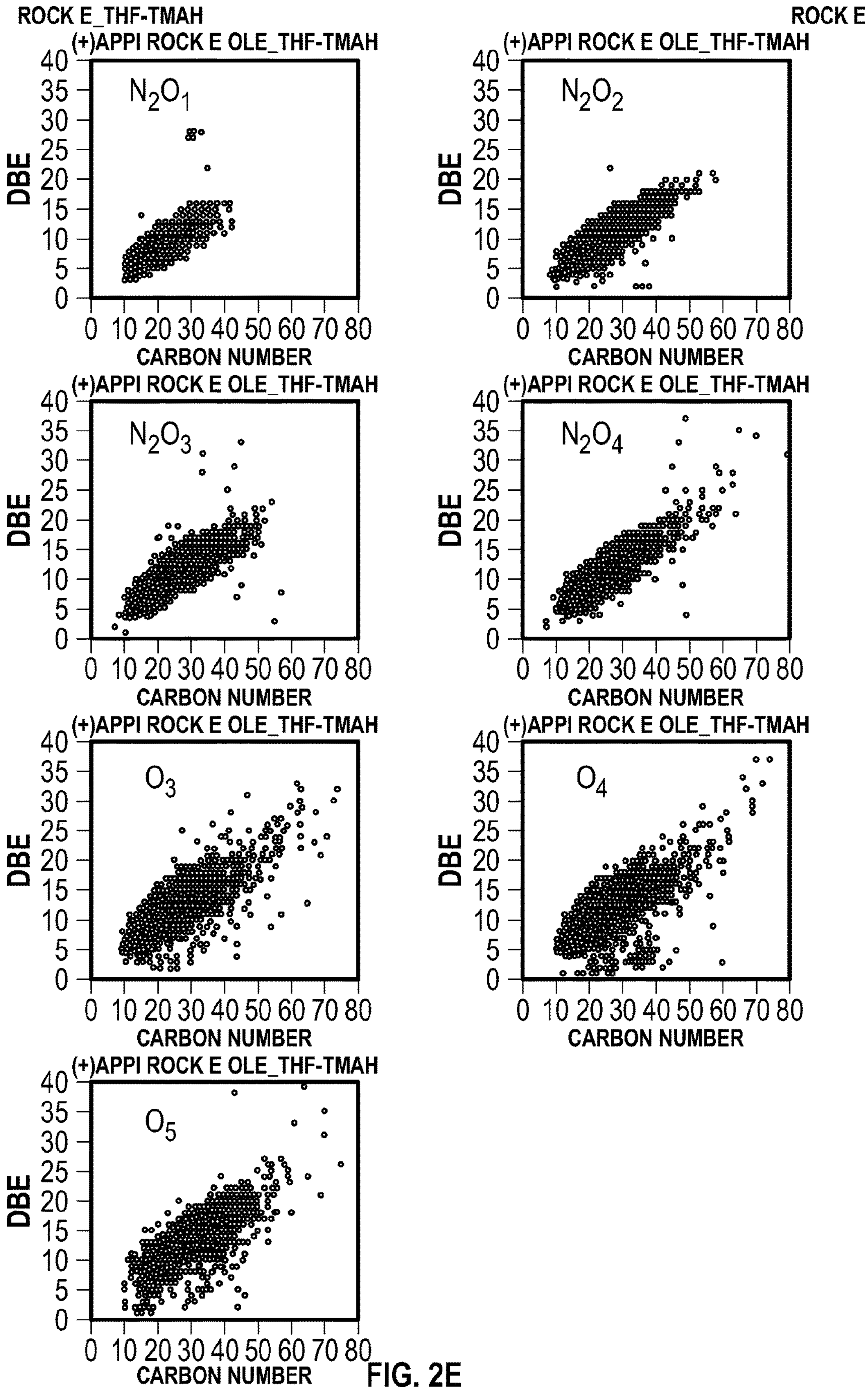

The following discussion is directed to various exemplary aspects. However, one skilled in the art will understand that the examples disclosed herein have broad application, and that the discussion of any aspect is meant only to be exemplary of that aspect, and not intended to suggest that the scope of the disclosure, including the claims, is limited to that aspect.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ."

Disclosed herein are methods and compositions for use in EOR. In one or more aspects, the presently disclosed methods and compositions are for use in assessing the potential of a reservoir to yield additional natural resources (e.g., hydrocarbons) by flooding the reservoir with a low salinity fluid. The methods and compositions disclosed herein may provide one or more indicators that a reservoir, which previously produced a natural resource, such as a hydrocarbon, may provide an additional amount of that natural resource when treated with a low salinity fluid. In such aspects, the additional resources obtained from treatment with a low salinity fluid may range from about 1% to about 20% of the original amount of resources obtained from the reservoir or the original amount of oil in place (OOIP). Alternatively, the additional resources may be recovered in an amount of greater than about 1%, alternatively greater than about 5%, alternatively greater than about 10% or alternatively greater than about 15% of the OOIP based on total weight of OOIP. It is to be understood, the methods disclosed herein are utilized in wellbores or formations that previously had resources removed utilizing other methods (e.g., high salinity water flooding). Herein, the methods and compositions disclosed assess the Low Salinity Response (LSR) of the wellbore or formation.

Herein, the term "low salinity fluid" refers to a fluid (e.g., aqueous fluid) having a total dissolved solids (TDS) content of less than about 20,000 parts per million volume (ppmv), alternatively less than about 15,000 ppmv, or alternatively less than about 10,000 ppmv. Herein, the TDS refers to a measure of the dissolved combined content of all inorganic and organic substances present in a liquid in molecular, ionized, or micro-granular suspended form.

In one or more aspects, the low salinity fluid is a low salinity water having a TDS content in the range of from about 200 ppmv to about 10,000 ppmv, alternatively from about 500 ppmv to about 10,000 ppmv, alternatively from about 500 ppmv to about 7,500 ppmv, or alternatively from about 500 ppmv to about 5,000 ppmv.

The low salinity aqueous fluid may be a fresh water or a brackish water. Fresh water may be obtained from a river, lake, or an aquifer, and have a TDS content of less than about 1,500 ppm. Brackish water may be obtained from an estuarine river source, an inland sea, or an aquifer. In addition, certain produced waters may be of sufficiently low salinity that they may be employed as the low salinity water. Alternatively, the low salinity water may be a desalinated water produced by a desalination plant, such as a desalination plant employing a membrane desalination process such as reverse osmosis or forward osmosis (also referred to as direct osmosis) process. Waters that may be used as feed to a membrane desalination plant include seawater, brackish waters (for example, estuarine, aquifer or produced waters), saline aquifer waters, saline-produced waters or a combination thereof. The use of produced water as a feed to the desalination plant is advantageous in locations where there are restrictions on disposal of produced water. Seawater may also be a suitable feed water for a desalination plant. In such aspects, suitable seawater may be characterized as being inland seas having from about 15,000 ppmv to about 40,000 ppmv TDS, or oceanic seas, having from about 30,000 ppmv to 45,000 ppmv TDS.

An aspect of a method of the present disclosure is depicted in FIG. 1. In an aspect, a method for assessing the LSR of a reservoir, 100, comprises obtaining a sample of the reservoir or formation of interest. Such reservoir samples may be termed formation core samples or reservoir plugs.

Formation core samples may be acquired using any suitable methodology. For example, a formation core sample may be obtained by actuating a formation coring tool in a subterranean wellbore. The formation core sample may be retrieved to the surface. The formation core sample acquired may include any suitable formation core sample. For example, the formation core sample may include a fresh state formation core sample. By "fresh state" it is meant that the formation core sample is in an "as received" condition not having undergone sample preparation procedures such as cleaning, oil or brine flushing or re-saturation, and/or aging with various reservoir fluids. In an aspect, the formation core sample may comprise any number of minerals including but not limited to quartz, kaolinite, illite, mica, smecite, chlorite, feldspar, plagioclase, calcite, or a combination thereof.

In an aspect, the method further comprises crushing the formation core sample, 10, using any suitable methodology to form a crushed formation core sample. The method may further comprise washing the crushed formation core sample with a first series of solvents to form a first series of solvent extracts. In an aspect, the first series of solvents comprise a nonpolar solvent having a relative polarity of less than about 2.0, alternatively from about 0.0 to about 2.5 or alternatively from about 0.0 to about 2.0. In an aspect, the crushed formation core sample is washed with a nonpolar solvent selected from the group consisting of cyclohexane, pentane, heptane, hexane, carbon tetrachloride, carbon disulfide, p-xylene, toluene, benzene, ether, methyl-t-butyl ether, diethylamine, dioxane, and a combination thereof. In one or more aspects, the crushed formation core sample is washed with xylene, 20. The crushed formation core sample may be washed a plurality of times, denoted n, to generate n xylene wash samples where n ranges from 2 to 20, alternatively from 2 to 15 or alternatively from 2 to 10. In one or more aspects, n is 9. The xylene wash samples may each be each stored separately in a suitable container. In an aspect, the crushed formation core sample having been subjected to washing with a nonpolar solvent is termed a "washed, crushed" formation core sample. For each aspect disclosed herein, washing of a material, extraction of a material or contacting of a material (e.g., core formation sample) with a solution (e.g., solvent, treating fluid) may be carried out for any suitable time period, for example for from about 1 minute to about 60 minutes, alternatively from about 1 minute to about 20 minutes or alternatively from about 1 minute to about 5 minutes.

The activity disclosed (e.g., washing, extraction) may be carried out under ambient conditions (e.g., room temperature and pressure) in any suitable vessel or container. Means of agitating the materials that are being contacted, washed, treated such as stirring or shaking may be employed as is suitable. As would be understood by one of ordinary skill in the art, contacting of a formation core sample (solid) with any solution (e.g., solvent) results in a solid-liquid mixture that may be separated using any suitable methodology (e.g., gravity separation, centrifugation, filtration).

In an aspect, the method further comprises washing the washed, crushed formation core sample with a polar solvent. 30. In an aspect, the polar solvent has a relative polarity of greater than about 3.5, alternatively from about 3.6 to about 8.0, or alternatively from about 4.0 to about 8.0. In an aspect, the washed crushed formation core sample is washed with a polar solvent such as a $C_1$ to $C_{10}$ alcohol, or alternatively, a $C_1$ to $C_5$ alcohol. In some aspects, the alcohol can be methanol, ethanol, propanol, butanol, n-propanol, iso-propanol, n-butanol, tert-butanol, or a combination thereof. In an aspect, the polar solvent is selected from the group consisting of dimethyl sulfoxide, acetonitrile, 3-pentanol, 2-pentanol, butanol, cyclohexanol, 1-octanol, 2-propanol, 1-heptanol, acetone, diethylene glycol, methanol, ethanol, propanol, butanol, n-propanol, iso-propanol, n-butanol, tert-butanol, and a combination thereof. In one or more aspects, the washed crushed formation core sample is washed with methanol. Washing of the washed, crushed formation core sample may be carried out a plurality of times, denoted n, to generate n methanol wash samples where n ranges from 2 to 20, alternatively from 2 to 15, or alternatively from 2 to 10. In one or more aspects, n is 9. The polar wash samples (e.g., wash methanol) may be each stored separately in a suitable container. In an aspect, the washed crushed formation core sample having been subjected to washing with the polar solvent, as described herein, is termed an "extracted" formation core sample.

In an aspect, the extracted formation core sample, is subject to treatment with a series of treating solutions. In an aspect, the extracted formation core sample is contacted with a first treating solution comprising a solvent having a relative polarity of from about 3.5 to about 4.5, alternatively from about 3.5 to about 4.2 or alternatively about 4.0, 40. In an aspect, the first treating solution comprises an aprotic solvent, alternatively an aliphatic cyclic ether. In an aspect, the first treating solution comprises dimethyl ether, diethyl ether, a dipropyl ether, a dibutyl ether, methyl ethyl ether, a methyl propyl ether, a methyl butyl ether, tetrahydrofuran, a substituted tetrahydrofuran, a dihydrofuran, a substituted dihydrofuran, 1,3-dioxolane, a substituted 1,3-dioxolane, tetrahydropyran, a substituted tetrahydropyran, a dihydropyran, a substituted dihydropyran, pyran, a substituted pyran, a dioxane, a substituted dioxane, or a combination thereof. In an aspect, the first treating solution comprises tetrahydrofuran. The extracted formation core sample may contacted with the first treating solution a plurality of times, denoted n, to generate n first treated samples where n is ranges from 1 to 10, alternatively from 1 to 5 or alternatively from 2 to 5. In one or more aspects, n is 2. Each contact of the first treating solution with the extracted formation core generates a first treated solution which may each be stored separately in a suitable container. The extracted formation core sample after contact with the first treating solution is termed a treated formation core sample.

In an aspect, the method of the present disclosure further comprises contacting the treated formation core sample with a second treating solution comprising a solvent and an acid, 50. In an aspect, the solvent in the second treating solution is the same as the solvent in the first treating solution. Alternatively, the solvent in the second treating solution has a relative polarity index in the range disclosed for the solvent in the first treating solution but otherwise differs from the solvent of the first treating solution. In an aspect, the second treating solution comprises tetrahydrofuran. In an aspect, the second treating solution also comprises an acid. In an aspect, the second treating solution comprises formic acid, acetic acid, propanic acid, butanoic acid, citric acid, or a combination thereof. Alternatively, the second treating solution comprises formic acid. The second treating solution may contain a ratio of solvent to acid ranging from about 0.5 weight percent (wt. %) to about 20 wt. %, alternatively from about 0.5 wt. % to about 10 wt. %, or alternatively from about 0.5 wt. % to 2 wt. % based on the total weight of the treating solution.

The treated formation core sample may be contacted with the second treating solution a plurality of times, denoted n, to generate n twice-treated samples where n ranges from 1 to 10, alternatively from 1 to 5 or alternatively from 2 to 5. In one or more aspects, n is 2. The treated formation core sample having been contacted with a second treating solution is termed a "twice-treated" formation core sample (2×FCS). Each contact of the second treating solution with the treated formation core generates a twice-treated solution which may each be stored separately in a suitable container.

In an aspect, a method of the present disclosure further comprises contacting the 2×FCS with the first treating solution, 60. The 2×FCS may be contacted with the first treating solution a plurality of times, denoted n, to generate n washed 2×FCS where n ranges from 1 to 10, alternatively from 1 to 5, or alternatively from 2 to 5. In one or more aspects, n is 2. The 2×FCS having been contacted with the first treating solution is termed a washed twice-treated formation core sample (W-2×FCS). Each contact of the first treating solution with the 2×FCS results in a washed twice-treated sample which may each be stored separately in a suitable container.

In an aspect, a method of the present disclosure further comprises contacting the W-2×FCS with a third treating solution comprising a solvent and a base, 70. In an aspect, the solvent in the third treating solution is the same as the solvent in the first treating solution. Alternatively, the solvent in the third treating solution has a relative polarity index in the range disclosed for the solvent in the first treating solution but otherwise differs from the solvent of the first treating solution. In an aspect, the third treating solution comprises tetrahydrofuran, In an aspect, the third treating solution further comprises a base. Nonlimiting examples of bases suitable for use in the third treating solution includes potassium hydroxide, sodium hydroxide, pyridine, alkanamines, imidazole, benzimidazole, histidine, guanidine, phosphazene, hydroxides of quaternary ammonium cations, or a combination thereof. Alternatively, the third treating solution comprises tetramethylammonium hydroxide (TMAH) as the base. The third treating solution may contain a ratio of solvent to base ranging from about 0.5 wt. % to about 20 wt. %, alternatively from about 0.5 wt. % to about 10 wt. %, or alternatively from about 0.5 wt. % to about 2 wt. %. Each contact of the third treating solution with the W-2×FCS generates an extraction solution, which may each be stored separately in a suitable container. The W-2×FCS may be contacted with the third treating solution a plurality of times, denoted n, to generate n extraction samples where n ranges from 1 to 10, alternatively from 1 to 5 or alternatively from 2 to 5. In one or more aspects, n is 2. The W-2×FCS once treated with the third treating solution results in a depleted formation core sample.

In an aspect, the method further comprises subjecting the extraction samples to analysis by mass spectrometry to determine the amount of catecholamine type structures (CTS) present in the extraction samples, 80. Herein, CTS refers to molecules having the general formula $C_xH_yN_mO_{x-3}$ where x is from about 10 to about 30, y is from about 22 to about 62, and m is from about 1 to about 2. In an alternative aspect, the CTS refers to molecules having the general formula $C_xH_yO_{x-3}$ where x is from about 10 to about 30 and y is from about 22 to about 62. In a further aspect, the CTS has a double bond equivalent (DBE) ranging from about 2 to about 10, alternatively from about 2 to about 8, or alternatively from about 2 to about 6. The DBE, also termed the Degree of Unsaturation (DoU) or the extent of Hydrogen insufficiency, refers to the level of unsaturation or the amount of pi electrons present in the molecule. The DBE can be calculated utilizing formula (1);

$$DBE=C-(H/2)+(N/2)+1 \quad \text{Formula 1}$$

where C is the number of carbon atoms, N is the number of nitrogen atoms, and H is the number of hydrogen atoms.

Without being limited by theory, CTS molecules having the general structure disclosed herein may function to compatibilize the interface of formation surfaces with hydrocarbons located within the formation thus stabilizing the resource-rock interaction and reducing the LSR. In an aspect, the relative abundance of CTS in the extraction samples may be determined by any suitable methodology. For example, the relative abundance of CTS may be determined by mass spectrometry, alternatively high resolution mass spectrometry, alternatively high resolution mass spectrometry with an atmospheric phase photoionization mode (APPI).

Mass spectrometry (MS) is an analytical chemistry technique that helps identify the amount and type of chemicals present in a sample. Mass spectrometry works by ionizing chemical compounds to generate charged molecules or molecule fragments and measuring their mass-to-charge ratios. A mass spectrum (plural spectra) is a plot of the ion signal as a function of the mass-to-charge ratio. From spectra, the mass of the molecular ion and fragments are used to determine the elemental composition or isotopic signature of a compound and this information is used to elucidate the chemical structures of molecules. In APPI the principle is to use photons to ionize gas-phase molecules. After vaporization, the analyte interacts with photons emitted by a discharge lamp. These photons induce a series of gas-phase reactions that lead to ionization of the sample molecules. Several APPI sources have been developed and are commercially available.

The direct ionization of an analyte is generally characterized by a weak efficiency. This can be partially explained by the solvents which can absorb photons producing photoexcitation without ionization. The result is a reduction in the number of photons available for the direct ionization of the target compound, thus reducing the ionization efficiency. Thus, two distinct APPI sources are contemplated for use in analysis of the extraction samples; direct APPI and dopant APPI.

In an aspect, the LSR is proportional to the relative abundance of extractable CTS in the reservoir as determined by the amount of CTS in the extraction samples. Generally, the higher the amount of CTS present in the extraction samples the greater the tendency for the formation to yield additional natural resources (e.g., hydrocarbons) when treated with a low salinity water (i.e., high potential for a LSR).

In one or more aspects, the present of extractable CTS in the reservoir is indicative of the strength of the interaction between the crude oil and the mineral surface in the reservoir rock. In oil field applications, the fluid phases may be water, oil, and/or gas while the solid phase may be the minerals that make up the reservoir rock. The crude oil is "anchored" on the mineral surface due to the interaction between the polar compounds in the crude oil and the mineral surface. CTS is a group of organic molecules with the following structural characteristics: (1) an aromatic "core" which consists of one or more aromatic rings; (2) the presence of four or more functional groups (e.g. —$NH_2$, —OH) on the aromatic "core", where each of these functional groups can form one or more hydrogen bonds with other polar compounds in the crude oil or the hydroxyl groups (—OH) on the mineral surface. As a result, CTS molecules can act as "anchoring points" to keep the crude oil on the mineral surface. On the other hand, CTS molecules have different interaction with different minerals, Kaolinite has a very strong interaction with CTS molecules while the interaction between other minerals and CTS is relatively weak. The capability of the injected low salinity brine to remove crude oil from the mineral surface is strongly dependent on the amount of the CTS on the mineral surface as well as the amount of kaolinite in the reservoir rock. If the amount of CTS on the mineral surface is low, then the oil "anchored" on the mineral surface is limited, and there is not much "anchored" oil to be removed from the mineral surface. As a result, introducing a low salinity brine to the reservoir will not result enhanced oil recovery from the rock. In other words, "low salinity brine FOR effect" is not observed in this rock or the rock would be expected to have a poor LSR. This can be attributed to a situation where the reservoir rock simultaneously has (1) a high abundance of CTS molecules on the rock surface, and (2) a high abundance of kaolinite mineral, the amount of "anchored oil" on the rock surface is high, but the "anchored oil" cannot be released by a low salinity brine (hence a poor LSR) because there are too many "anchoring points," which strongly keep the oil on the rock surface. In this case, the "low salinity brine FOR effect" cannot be observed. In another instance, the reservoir rock simultaneously has (1) a high abundance of CTS molecules on the rock surface, and (2) a low abundance of kaolinite mineral, the amount of "anchored oil" on the rock surface is high. In such instances, because the interaction between the CTS molecules and non-kaolinite minerals is weak, this weak interaction can be broken by the low salinity brine resulting in the weakly "anchored" oil being released by a low salinity brine. As a result, the "low salinity brine FOR effect" can be observed in this case or a good LSR.

The present disclosure provides for a "low salinity brine EOR response" of a reservoir rock being related to the relative abundance of extractable CTS present in the reservoir rock. The relative abundance of extractable CTS present in the reservoir rock may designated as "high" when a relative abundance of extractable CTS ranges in amount from about 25 mole percent (mol. %) to about 95 mol. %, alternatively from about 25 mol. % to about 90 mol. %, or alternatively from about 40 mol. % to about 90 mol. %, where the mole percentage is based on the total abundance of the ionizable species revealed by the Atmospheric Pressure Photoionization High Resolution Mass Spectrometry (APPI-HRMS). Alternatively, the relative abundance of extractable CTS may be designated as low when a relative abundance of extractable CTS is less than about 25 mol. % where the mole percentage is based on the total abundance of the ionizable species revealed by the Atmospheric Pressure Photoionization High Resolution Mass Spectrometry (APPI-HRMS).

Reservoir rock may comprise a variety compounds including, but not limited, to quartz, kaolinite, illite, mica, smecite, chlorite, feldspar, plagioclase, calcite, or a combination thereof. In an aspect, the method further comprises determining the amount of kalonite in the formation core sample.

Kaolinite refers to hydrous aluminum silicate clay with an extended sheet structure which can be regarded as having two constituents, a layer of tetrahedral $SiO_4$ and a layer of octahedral $OH^-$. The amount of kalonite in the reservoir core formation sample may be determined using any suitable methodology. For example, the amount of kalonite in the reservoir core formation sample may be determined by X-ray fluorescence analysis, X-ray diffraction analysis, scanning electron microscopy, or a combination thereof. In an aspect, the amount of kalonite in the reservoir core formation sample is inversely proportional to the LSR such that as the amount of kalonite in the reservoir core formation sample increases the LSR decreases. In an aspect, the reservoir core formation sample contains a low amount of kalonite. Herein, a "low" amount refers to from about 0 weight percent (wt. %) to about 5 wt. %, alternatively less than about 5 wt. % or alternatively less than about 1 wt. % based on X-Ray Diffraction (XRD) analysis.

In an aspect, the methods of the present disclosure may be utilized in order to determine the potential for a reservoir to produce additional resources such as hydrocarbons. In such aspects, a formation core sample is obtained and treated as disclosed herein to obtain extraction samples and the percentage kalonite in the formation. In an aspect, the formation core sample provides extraction samples having CTS in a relative abundance ranging from about 20 wt. % to about 90 wt. %, alternatively from about 40 wt. % to about 80 wt. % or alternatively from about 50 wt. % to about 80 wt. %. Additionally, the formation core may have an amount of kalonite of less than about 2 wt. %, alternatively less than about 1 wt. %, or alternatively less than about 0.5 wt. %. In such aspects, the formation would be expected to exhibit a positive LSR wherein flooding of the formation with a low salinity water produces from about 0.1% to about 20% of the OOIP (e.g., hydrocarbons), alternatively from about 1% to about 15% of the OOIP, or alternatively from about 5% to about 15% of the OOIP In an aspect, a reservoir, being assessed as disclosed herein, is found to have a positive LSR. The methods of this disclosure may further comprise subjecting the hydrocarbon-bearing layer of the reservoir to a low salinity waterflood. In some aspects, the method comprises (and/or a control system is programmed to provide) injection of the low salinity injection fluid into the oil-bearing layer of the reservoir.

The low salinity injection water can be produced and the low salinity waterflood effected via any suitable methodology. In sandstone reservoirs, depending on the content and composition of clays in the formation rock, injection of a low salinity water may result in loss of injectivity. This loss of injectivity arises from formation damage in the near wellbore region of the injection well caused by swelling and migration of clays.

U.S. Pat. No. 3,208,528 teaches the phenomenon of loss of permeability ("clay blocking") when clays or other mineral fines become dispersed by fresh water, and the dispersed particles bridge to partially dam interstices in the rock. In such aspects, treating a water-sensitive formation by varying the salinity of the injection water such that the salt content in the injected water is reduced gradually or in step-wise fashion while maintaining constant the ratio of total salt concentration to divalent cation salt concentration until the salt concentration in the water being injected has reached the desired degree of dilution can mitigate the risk of formation damage. Thus, this stepped or gradual reduction in salinity may be utilized to mitigate the risk of "salinity shock" and of permeability damage leading to a loss of injectivity. Accordingly, in some aspects, injection of low salinity water can be performed by gradually reducing a salinity of the injection water aqueous injection fluid to a desired salinity for a main phase.

In some aspects, the methods of the present disclosure result in more effective EOR due to the ability to assess the LSR of a formation and specifically determine if the formation has a CTS and kalonite content that indicates a positive LSR.

EXAMPLES

The aspects having been generally described, the following examples are given as particular aspects of the disclosure and to demonstrate the practice and advantages thereof. It is understood that the examples are given by way of illustration and are not intended to limit the specification or the claims in any manner.

The methods disclosed herein were used to assess the LSR of different rock formations. Six formation samples were obtained. Sample A was a preserved reservoir rock which was produced from Reservoir 1, and was filled with crude oil (Oil 1). The rock matrix in Sample A is called "Rock 1". Sample B was another reservoir rock ("Rock 2") which has been solvent cleaned, then aged with Oil I at reservoir conditions; subsequently the rock was waterflooded with low salinity brine and then solvent cleaned. Sample C was an outcrop rock ("Rock 3") which has been solvent cleaned, then aged with Oil I at reservoir conditions; subsequently it was waterflooded with low salinity brine, and solvent cleaned. Sample D was the same outcrop rock ("Rock 3") which has been solvent cleaned, then aged with Oil A at reservoir conditions, then it was waterflooded with high salinity brine first; subsequently it was further waterflooded with low salinity brine, and solvent cleaned. Sample E was a preserved reservoir rock which was produced from Reservoir II, and was filled with crude oil (Oil II). The rock matric in Sample E is called "Rock 4". Sample F was another preserved reservoir rock which was produced from Reservoir II, and was waterflooded using low salinity brine and then solvent cleaned. The rock matrix in Sample F is also "Rock 4". Details of the procedure of rock aging, the Reservoir Condition waterflooding, as well as the solvent cleaning process can be found in previous publication: Webb, K., Lager, A. and Black C., Comparison of High/Low Salinity Water/Oil Relative Permeability, presented at the International Symposium of the Society of Core Analysts, Abu Dhabi, UAE, Oct. 29-Nov. 2, 2008.

Samples A through F were crushed and then each sample was subjected to nine rounds of xylene extraction followed by methanol extractions. The samples were then extracted sequentially (i) twice with tetrahydrofuran (THF), (ii) twice with a THF-acid solution, (iii) twice with THF and finally (iv) twice with a THF-base solution. The samples following extraction with a THF-base solution were subjected to high resolution mass spectrometry-APPI. The mass spectra are presented in FIG. 2.

Figure 3:
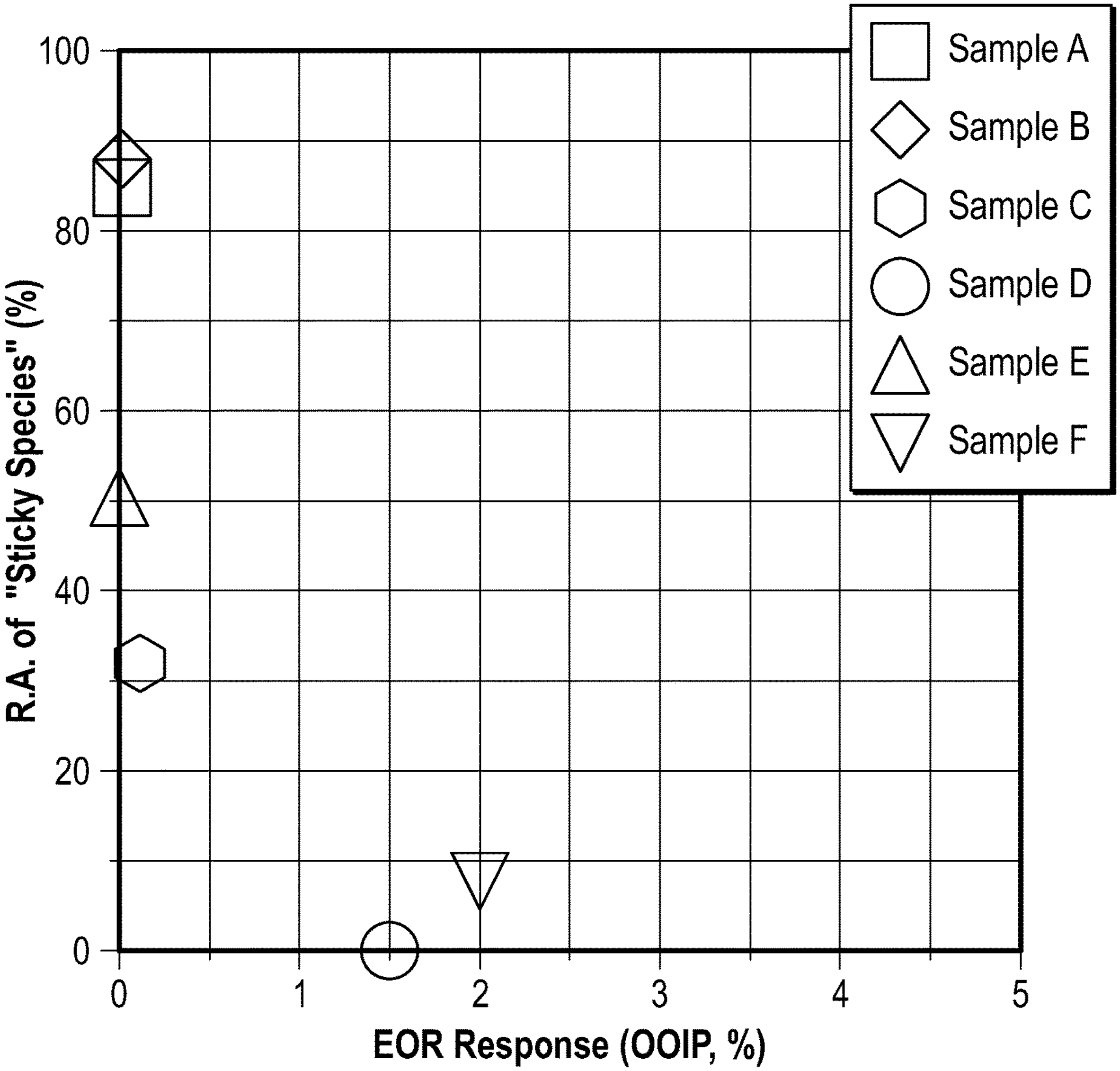
FIG. 3 is a plot of original oil in place as a function of the amount of catecholamine type structures.

The EOR response in terms of OOIP were determined for Samples A-F are presented as a graph of relative abundance of CTS, FIG. 3.

Rock 1, Rock 2, Rock 3 and Rock 4 were further analyzed by X-ray diffraction and the minerology of these samples are presented in Table 1.

TABLE 1

| | Rock 1 | Rock 2 | Rock 3 | Rock 4 |
|---|---|---|---|---|
| Quartz | 86.1 | 89.1 | 95.7 | 95.6 |
| Kaolinite | 4.9 | 10.9 | 2.4 | 0.2 |
| Illite + Mica | 3.7 | 0.0 | 0.2 | 0.4 |
| Smectite | 0.0 | 0.0 | 0.0 | 1.1 |
| Chlorite | 0.0 | 0.0 | 0.0 | 0.2 |
| K Feldspar | 3.6 | 0.0 | 1.1 | 2.6 |
| Plagioclase | 1.7 | 0.0 | 0.6 | 0.0 |
| Calcite | 0.0 | 0.0 | 0.0 | 0.0 |
| Clay_Wt. %_<2 um | 2.1 | 1.5 | 2.3 | 2.1 |

The results demonstrate that the sample having the worst LSR, Sample A, also had the highest percentage kalonite while the sample having the best LSR, Sample F, had the lowest percentage kalonite.

While various aspects have been shown and described, modifications thereof can be made by one skilled in the art without departing from the spirit and teachings of the disclosure. The aspects described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, RL and an upper limit, RU is disclosed, any number falling within the range is specifically disclosed. In particular, the following numbers within the range are specifically disclosed: R=RL+k*(RU−RL), wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an aspect of the present disclosure. Thus, the claims are a further description and are an addition to the aspects of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

ADDITIONAL DESCRIPTION

The particular aspects disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative aspects disclosed above may be altered or modified and all such variations are considered within the scope and spirit of the present disclosure. Alternative aspects that result from combining, integrating, and/or omitting features of the aspect(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Aspects disclosed herein include:

A first aspect which is a method of assessing the response of a reservoir rock to low salinity water comprising obtaining a formation core sample of a reservoir rock from a reservoir; sequentially washing the formation core sample with a first series of solvents to form a first series of solvent extracts and an extracted formation core sample; sequentially washing the extracted formation core sample with a second series of solvents to form a second series of solvent extracts and a cleaned formation core sample; generating a series of mass spectra of the second series of solvent extracts, wherein the relative abundance of the catecholamine-type structures (CTS) is determined using the series of mass spectra; subjecting the formation core sample to analysis by X-ray diffraction to generate a diffraction pattern, wherein the relative abundance of kalonite is determined using the diffraction pattern; and assessing a response of the reservoir rock to low salinity water based on the percentage of kalonite and the relative abundance of CTS.

A second aspect which is the method of the first aspect wherein the CTS comprises compounds having a general formula $C_xH_yN_mO_{3-x}$ where x is from about 10 to about 30, y is from about 22 to about 62, and m is from 1 to 2.

A third aspect which is the method of any of the first through second aspects, wherein the CTS comprises compounds having a general formula $C_xH_yO_{3-x}$ where x is from about 10 to about 30, y is from about 22 to about 62, and m is from 1 to 2.

A fourth aspect which is the method of any of the first through third aspects, wherein the CTS has a double bond equivalent of from about 2 to about 10.

A fifth aspect which is the method of any of the first through fourth aspects wherein the reservoir rock comprises quartz, kaolinite, illite, mica, smecite, chlorite, feldspar, plagioclase, calcite, or a combination thereof.

A sixth aspect which is the method of any of the first through fifth aspects wherein the first series of solvents comprises a nonpolar solvent and a polar solvent.

A seventh aspect which is the method of any of the first through sixth aspects wherein the second series of solvents comprises a compound having a polarity index ranging from about 0.175 to about 0.300.

An eighth aspect which is the method of any of the first through seventh aspects wherein the second series of solvents comprise an aprotic solvent.

A ninth aspect which is the method of any of the first through eighth aspects wherein the second series of solvents comprises an aliphatic cyclic ether.

A tenth aspect which is the method of the ninth aspect wherein the aliphatic cyclic ether comprises dimethyl ether, diethyl ether, a dipropyl ether, a dibutyl ether, methyl ethyl ether, a methyl propyl ether, a methyl butyl ether, tetrahydrofuran, a substituted tetrahydrofuran, a dihydrofuran, a substituted dihydrofuran, 1,3-dioxolane, a substituted 1,3-dioxolane, tetrahydropyran, a substituted tetrahydropyran, a dihydropyran, a substituted dihydropyran, pyran, a substituted pyran, a dioxane, a substituted dioxane, or a combination thereof.

An eleventh aspect which is the method of any of the first through tenth aspects wherein the second series of solvents comprise tetrahydrofuran.

A twelfth aspect which is the method of any of the first through eleventh aspects wherein the second series of solvents comprises an acid or a base.

A thirteenth aspect which is the method of the twelfth aspect the acid comprises, formic acid, acetic acid, propanic acid, butanoic acid, citric acid, or a combination thereof.

A fourteenth aspect which is the method of the twelfth aspect wherein the acid comprises formic acid.

A fifteenth aspect which is the method of the twelfth aspect wherein the base comprises potassium hydroxide, sodium hydroxide, pyridine, alkanamines, imidazole, benzimidazole, histidine, guanidine, phosphazene, hydroxides of quaternary ammonium cations, or a combination thereof.

A sixteenth aspect which is the method of the twelfth aspect wherein the base comprises tetramethylammonium hydroxide.

A seventeenth aspect which is the method of any of the first through sixteenth aspects wherein the high resolution mass spectrometry comprises a atmospheric phase photoionization mode.

An eighteenth aspect which is a method of enhanced oil recovery from a resource-containing reservoir zone comprising obtaining a rock sample from the resource-containing reservoir zone; contacting the rock sample with solvents sequentially to form solvent extracts and a cleaned rock sample; subjecting the cleaned rock sample to X-ray diffraction wherein X-ray diffraction identifies a percentage kaolinite of the cleaned rock sample: subjecting the solvent extracts to mass spectrometry wherein the mass spectrometry identifies a percentage catecholamine-type structures (CTS) in at least one of the solvent extracts; and determining the reservoir rocks with high possibility of carrying positive response to low salinity water enhanced oil recovery method based on the percentage of kaolinite and the percentage of CTS.

A nineteenth aspect which is the method of the eighteenth aspect further comprising injecting into the resource-containing reservoir zone a fluid having a salinity of from about 1400 ppm to about 5000 ppm when a percentage of kaolinite is from about 0 wt. % to about 2 wt. % and a CTS is present in an amount of from about 40 mol. % to about 90 mol. % as determined by high resolution mass spectrometry using atmospheric phase photoionization mode.

A twentieth aspect which is the method of any of the eighteenth through nineteenth aspects wherein the high resolution mass spectrometry comprises an atmospheric phase photoionization mode.

A twenty-first aspect which is the method of any of the eighteenth through twentieth aspects wherein the CTS comprises compounds having a general formula $C_xH_yN_mO_{3-x}$ where x is from about 10 to about 30, y is from about 22 to about 62, and m is from 1 to 2.

A twenty-second aspect which is the method of any of the eighteenth through twenty-first aspects wherein the CTS comprises compounds having a general formula $C_xH_yO_{3-x}$ where x is from about 10 to about 30, y is from about 22 to about 62, and m is from 1 to 2.

A twenty-third aspect which is the method of any of the eighteenth through twenty-second aspects, wherein the CTS has a double bond equivalent of from about 2 to about 10.

A twenty-fourth aspect which is the method of any of the eighteenth through twenty-third aspects wherein the HRMS comprises an atmospheric phase photoionization mode.

While aspects of the disclosure have been shown and described, modifications thereof can be made by one skilled in the art without departing from the teachings of this disclosure. The aspects described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the detailed description of the present invention. The disclosures of all patents, patent applications, and publications cited herein are hereby incorporated by reference.

What is claimed is:

1. A method of assessing the response of a reservoir rock to low salinity water comprising:

obtaining a formation core sample of a reservoir rock from a reservoir;

sequentially washing the formation core sample with a first series of solvents comprising a nonpolar solvent followed by a polar solvent to form a first series of solvent extracts and an extracted formation core sample;

sequentially washing the extracted formation core sample with a treating solution to form a second series of solvent extracts and a cleaned formation core sample;

generating a series of mass spectra of the second series of solvent extracts, wherein the relative abundance of catecholamine-type structures (CTS) is determined using the series of mass spectra, wherein the CTS is selected from the group consisting of compounds having a general formula $C_xH_yN_mO_{x-3}$ where x is from about 10 to about 30, y is from about 22 to about 62, and m is from 1 to 2 and compounds having a general formula $C_xH_yO_{x-3}$ where x is from about 10 to about 30, and y is from about 22 to about 62;

subjecting the formation core sample to analysis by X-ray diffraction to generate a diffraction pattern, wherein the relative abundance of kalonite is determined using the diffraction pattern; and assessing a response of the reservoir rock to low salinity water based on the percentage of kalonite and the relative abundance of CTS, wherein the reservoir rock having a CTS of greater than 25 mol % produces an additional 0.01% to 20% amount of the original oil in place when contacted with low salinity water.

2. The method of claim 1, wherein the CTS has a double bond equivalent of from about 2 to about 10.

3. The method of claim 1, wherein the reservoir rock comprises a quartz, a kaolinite, an illite, a mica, a smecite, a chlorite, a feldspar, a plagioclase, a calcite, or a combination thereof.

4. The method of claim 1, wherein the treating solution comprises a compound having a polarity index ranging from about 0.175 to about 0.300.

5. The method of claim 1, wherein the treating solution comprises an aprotic solvent.

6. The method of claim 5, wherein the aliphatic cyclic ether comprises a dimethyl ether, a diethyl ether, a dipropyl ether, a dibutyl ether, a methyl ethyl ether, a methyl propyl ether, a methyl butyl ether, a tetrahydrofuran, a substituted tetrahydrofuran, a dihydrofuran, a substituted dihydrofuran, a 1,3-dioxolane, a substituted 1,3-dioxolane, a tetrahydropyran, a substituted tetrahydropyran, a dihydropyran, a substituted dihydropyran, pyran, a substituted pyran, a dioxane, a substituted dioxane, or a combination thereof.

7. The method of claim 1, wherein the treating solution comprises an aliphatic cyclic ether.

8. The method of claim 1, wherein the treating solution comprises tetrahydrofuran.

9. The method of claim 1, wherein the treating solution comprises an acid or a base.

10. The method of claim 9, wherein the acid comprises, formic acid, acetic acid, propanic acid, butanoic acid, citric acid, or a combination thereof.

11. The method of claim 9, wherein the acid comprises formic acid.

12. The method of claim 9, wherein the base comprises potassium hydroxide, sodium hydroxide, pyridine, alkanamines, imidazole, benzimidazole, histidine, guanidine, phosphazene, hydroxides of quaternary ammonium cations, or a combination thereof.

13. The method of claim 9, wherein the base comprises tetramethylammonium hydroxide.

14. The method of claim 1, wherein a high resolution mass spectrometry comprises an atmospheric phase photoionization mode.

15. A method of enhanced oil recovery from a resource-containing reservoir zone comprising:

obtaining a rock sample from the resource-containing reservoir zone;

contacting the rock sample with solvents sequentially to form solvent extracts and a cleaned rock sample;

subjecting the cleaned rock sample to X-ray diffraction wherein X-ray diffraction identifies a percentage kaolinite of the cleaned rock sample;

subjecting the solvent extracts to mass spectrometry wherein the mass spectrometry identifies a percentage catecholamine-type structures (CTS) in at least one of the solvent extracts, wherein the CTS compounds are selected from the group consisting of compounds having a general formula $C_xH_yN_mO_{x-3}$ where x is from about 10 to about 30, y is from about 22 to about 62, and m is from 1 to 2 and compounds having a general formula $C_xH_yO_{x-3}$ where x is from about 10 to about 30, and y is from about 22 to about 62;

determining the reservoir rocks with high possibility of carrying positive response to low salinity water enhanced oil recovery method based on the percentage of kaolinite and the percentage of CTS, wherein a high possibility of positive response is characterized by having a CTS of greater than 25 mol %; and initiating an enhanced oil recovery operation comprising placing low salinity water in the formation.

16. The method of claim 15, further comprising injecting into the resource-containing reservoir zone a fluid having a salinity of from about 1400 ppm to about 5000 ppm when a percentage of kaolinite is from about 0 wt % to about 2 wt % and a CTS is present in an amount of from about 40 mol % to about 90 mol % as determined by high resolution mass spectrometry using atmospheric phase photoionization mode.

17. The method of claim 15, wherein the mass spectrometry comprises an atmospheric phase photoionization mode.

18. The method of claim 15, wherein a CTS has a double bond equivalent of from about 2 to about 10.

19. The method of claim 15, wherein the mass spectrometry is a high resolution mass spectrometry (HRMS), and wherein the HRMS comprises an atmospheric phase photoionization mode.

* * * * *